United States Patent [19]

Moldowan

[11] Patent Number: 4,642,286

[45] Date of Patent: Feb. 10, 1987

[54] COMPOSITION AND METHOD FOR ETHANOL DETERMINATION

[76] Inventor: Mervin J. Moldowan, 480 Benton View Dr., Philomath, Oreg. 97370

[21] Appl. No.: 607,827

[22] Filed: May 7, 1984

[51] Int. Cl.⁴ .................... C12Q 1/26; C12Q 1/28; C12N 9/96; C12N 9/99

[52] U.S. Cl. .................................. 435/25; 435/28; 435/184; 435/188

[58] Field of Search ............... 435/25, 28, 188, 805, 435/810, 184

[56] References Cited

U.S. PATENT DOCUMENTS

| | | | |
|---|---|---|---|
| 2,990,338 | 6/1981 | Gibson | 435/25 |
| 3,493,467 | 2/1970 | Drell et al. | 435/26 |
| 3,962,037 | 6/1976 | Mitchell | 435/188 |
| 4,250,261 | 2/1981 | Eggeling et al. | 435/25 |
| 4,273,868 | 6/1981 | Walter | 435/28 |
| 4,281,062 | 7/1981 | Kallis | 435/28 |
| 4,315,002 | 2/1982 | Mauer | 435/188 |
| 4,430,427 | 2/1984 | Hopkins | 435/188 |
| 4,447,527 | 5/1984 | Monte et al. | 435/188 |

FOREIGN PATENT DOCUMENTS

| | | |
|---|---|---|
| 3214939 | 2/1982 | Fed. Rep. of Germany . |
| 1286095 | 8/1972 | United Kingdom ............. 435/188 |

OTHER PUBLICATIONS

Janssen et al., Biochim. Biophys. Acta, 151: 330–342 (1968).

*Primary Examiner*—Esther M. Kepplinger

[57] ABSTRACT

A novel composition and method is disclosed for detecting or quantitatively determining the level of ethanol. This is a colorimetric method and analysis can be done by the visual method. The composition comprises an enzyme alcohol oxidase, a peroxide detecting system consisting of peroxidase and chemicals and chemicals to stabilize alcohol oxidase.

8 Claims, No Drawings

COMPOSITION AND METHOD FOR ETHANOL DETERMINATION

BACKGROUND OF THE INVENTION

The invention consists of a method to determine ethanol levels in all types of samples. This technique uses enzymes and chemicals to quantify or detect ethanol by visual means.

Chemical or enzymatic methods have been employed to determine ethanol content in biological fluids or breath after ingestion of ethanol. To do the analysis many of these methods require elaborate devices, a laboratory setting and special trained personnel. Described in previous patents (for example U.S. Pat. No. 3,223,488) some inventions permit an immediate visual approximation of blood ethanol from a breath ethanol sample which can be used by a chemical untrained person. The formerly patented devices used various chemicals such as potassium chromate to react with ethanol which resulted in a color change. The intensity of the color change or the time required for the ethanol sensitive chemical to change color was used to estimate the level of ethanol in the person's breath which in turn was used to estimate the blood ethanol. One severe disadvantage for these chemical methods is that they are not specific for ethanol and many substances present in biological samples but not in breath will interfere with the chemical test. Therefore these methods are useful to directly analyze breath samples but not other types of biological samples. The present invention describes a method that can directly analyze for ethanol in most biological samples because it is specific for ethanol and interfering substances are not present in sufficient levels in these samples to interact.

Some devices used to collect breath for the estimation of ethanol can be done by untrained personnel although it is complicated and cumbersome to use which can result in serious blood ethanol error approximations. The source of the error is that the device collects and analyzes all respiratory air while accurate blood ethanol estimates are based on alveolar ethanol levels. The invention in this disclosure describes a device that will permit quick blood ethanol estimation without this source of error.

An alternate method to chemical estimation of ethanol is the use of enzymes and chemicals. The technique has been used as a tool for analysis of many diverse chemicals. One enzyme that has been employed for the detection of ethanol is alcohol dehydrogenase (ADH). Patents describing various methods using ADH have been published (U.S. Pat. No. 3,941,659) but these methods required chemical trained individuals and laboratory equipment. The ADH method must be reduced to a simpler method before it is accessible to most individuals for ethanol analysis.

Alcohol oxidase, another enzyme has been reported to react with ethanol. This enzyme will react with substances in addition to ethanol however they are not in sufficient concentration in biological samples to interfere with ethanol analysis. In some biological samples this enzyme can be used for analysis of these chemicals. The reaction between ethanol and alcohol oxidase along with oxygen has produced hydrogen peroxide and acetaldehyde. The reaction that takes place is:

Three methods have used the above reaction to quantify ethanol. One method measured the formation of hydrogen peroxide while another method measured the amount of oxygen used in the above reaction and the third method measured the amount of acetaldehyde produced. Hydrogen peroxide can be quantified by using O-dianisidine, a colorless dye. This dye has been reported to react with hydrogen peroxide to form a colored oxidized product. The reaction was catalyzed by the enzyme peroxidase and was quantified by a spectrophotometer to determine the quantity of ethanol. The principle reaction underlying the invention in this disclosure is the measurement of hydrogen peroxide produced. This method and other methods that use alcohol oxidase to estimate ethanol levels are known but they are batch type operations that require fresh enzyme, laboratory instruments and chemical trained personnel. The device described in this disclosure has been reduced to a simple method that can be used by most individuals outside the laboratory setting using a stable alcohol oxidase enzyme. This aspect is the novelty of the device that is enhanced by a stable enzyme product. Previous to this report a method to stabilize alcohol oxidase at room temperature for months has not been available.

The availability of devices to estimate blood ethanol by visual methods use breath as the sample for ethanol analysis. A device is not presently available to directly detect or quantify ethanol in most biological samples without laboratory instruments. However, such devices would be extremely useful and is described in this disclosure. The detection or the ability to quantify ethanol in body fluids such as saliva, urine or blood would be useful to a individual, law enforcement officer or dispensor of alcoholic beverages to determine ethanol intoxication by a quick objective test. Emergency medical diagnosis and treatment could be improved if blood ethanol levels could be determined quickly.

SUMMARY OF THE INVENTION

The present invention comprises a novel device and technique for detecting ethanol in all types of samples. The device consists of a absorbent paper that is impregnated with alcohol oxidase, peroxidase and other chemicals that are necessary for the device to detect ethanol and stabilize alcohol oxidase. This device can be inserted into a sample or a sample placed directly on the device. Within a short period of time the paper turns various shades of green. The change of color to green indicates the presence of alcohol while the intensity of the color indicates different levels of ethanol. The level of ethanol can be determined by visual means without the aid of instruments and a laboratory. This device is capable of estimating blood ethanol by a noninvasive method.

DETAILED DESCRIPTION OF THE INVENTION

The purpose of this invention is to provide a simple, inexpensive device to detect ethanol in fluids and breath. The device can detect or quantify ethanol by visual means which does not require specialized training or instruments. By direct analysis of salivary ethanol levels this test device can also be used as a noninvasive method to estimate ethanol blood levels. The analysis is quick and can be completed within minutes. This method should not be restricted to testing biological samples because the ethanol content of other samples could be detected and estimated (such as alocholic beverages).

This new method that is used to quantify ethanol can take many forms but the most common form is described in this disclosure. Strips of absorbent material, 0.5 cm. wide are attached to plastic sheets approximately 5 cm. long. The method for binding the above material can be done by chemical, thermal or adhesive tape. Using plastic sheets allowed less treated paper to be used for each assay leading to a reduced quantity of chemicals and enzyme per test.

The following indicator solution was used to impregnate the absorbent material and was applied at the rate of 0.5 ml. per 7 cm.$^2$ absorbent material. This rate of application can vary and is depdendant on the type of absorbent material or the strength of the indicator solution. The indicator solution composition is: O-tolidine 0.22% w/v, FDC YELLOW #5 dye 0.085% w/v, ethanol 50% w/v-Tris-phosphate buffer 0.6% w/v, pH 8.0 solution. Tris is the abbreviation for tris(hydroxymethyl)-aminomethane. The tris was adjusted to the proper pH with sodium phosphate before addition of ethanol. Tris-phosphate buffer maintains the proper pH range (7-9) for the optimum condition of the enzyme (alcohol oxidase) it's stability and catalytic activity. Dithiothreitol or ethylene diamine tetraacetic acid (EDTA) could be added to the above solution or to the solution containing the enzyme. The diethiothreitol 0.07% w/v acts as a stabilizer for alcohol oxidase while EDTA 0.017% w/v chelates some of the ions that could be present in the absorbent material. This ion if present in the reaction could inhibit the catalytic activity of alcohol oxidase. The absorbent material containing the above indicator solution is dried for 10 minutes at 75° C. Dependent on the type of absorbent material and the rate of application, the indicator composition range is: 0.002% to 20% w/v of ortho-tolidine, 0.001% to 50% w/v of dye, 0.5% to 95% of ethanol and 0.01% to 70% w/v of a buffer solution with a pH range between 5 and 10. The dye used with ortho-tolidine is FDC yellow No. 5.

The next step in preparing the ethanol detecting device is to apply the enzyme containing solution. The contents of this solution is: dextran (40,000 molecular weight) 7.5% w/v, sodium chloride 0.9% w/v, peroxidase (209 units) 0.15% w/v, alcohol oxidase (100 units, based on methanol assay) 0.195% w/v, semicarbazide HCL 0.0022% w/v, Tris-phosphate buffer (pH 8.0) 0.6% w/v. This solution is applied to the absorbent material containing the indicator. The rate of application is 0.5 ml. per 7 cm.$^2$ of absorbent material but this rate can vary considerably and result in an adequate detecting device. The material is air dried. The range for the content of the enzyme solution is: dextran 0.02% to 50% w/v, sodium chloride 0.02% to 20% w/v, peroxidase (95 units/mg) 0.001% to 20% w/v, alcohol oxidase (35 units/mg) 0.0001% to 40% w/v, semicarbazide hydrochloride 0.02% to 3% w/v and 0.01% to 75% w/v of a buffer solution with a pH range between 5 and 10. A unit of alcohol oxidase activity is defined as the amount of this enzyme that can oxidize 1.0 micromole of methanol to formaldehyde per minute at pH 7.5 at 25° C. Peroxidase is the catalyzing agent for O-tolidine and peroxide.

Listed are specific amounts for the indicator solution and the enzyme solution. The application rate for these solutions to absorbent paper is at the rate of 0.5 ml per 7 cm$^2$. The content of the indicator solution is: ortho-tolidine 0.10 g, FDC yellow No. 5 dye 0.042 g., 22 ml ethanol (95% V/V) and 23 ml buffer solution (pH 8.0). The enzyme solution content is 232 units peroxidase, 140 units alcohol oxidase, 0.15 g dextran, 0.018 g. sodium chloride, 0.0123 g. semicarbazide hydrochloride, and 2 ml buffer solution (pH 8.0). The enzyme alcohol oxidase is necessary for the catalsis of ethanol to acetaldehyde and hydrogen peroxide. This enzyme can be isolated from various sources the most common sources are from the yeast Pichia pastoris or Candida boidinii. Peroxidase is used to catalyze the reaction between hydrogen peroxide and O-tolidine to form the colored oxidized product. This enzyme is isolated from various sources that can be used although the most common is horseradish. The purpose of semicarbazide is to prevent extremely low levels of ethanol or other alcohol oxidase substrates to induce color changes and interfere with ethanol analysis. It is also used to sharply delineate color changes between selected ethanol concentrations and to stabilize the enzyme alcohol oxidase. For example using approximately 0.0033% w/v to 0.006% w/v semicarbazide provides a sharper differentiation between 80 mg% and 100 mg% ethanol. The above formulation containing the enzymes are useful to distinguish ethanol concentrations between 25 mg% to 150 mg%. Differentiation of ethanol levels at other concentrations can be detected by varying the alcohol oxidase concentration or the semicarbazide concentration. The principle underlying the use of semicarbazide is that it is a competitive inhibitor of alcohol oxidase. This means that higher concentrations of this chemical prevent lower concentrations of ethanol from reacting with alcohol oxidase. Therefore only higher concentrations of ethanol can be detected with higher levels of semicarbazide. However at these higher semicarbazide concentrations the test device becomes insensitive to lower ethanol levels. Results similar to semicarbazide can be accomplished with other inhibitors. Another purpose for semicarbazide is to bind acetaldehyde and prevent it's interaction with alcohol oxidase. The result is an improvement of the color reaction. Detran having various molecular weights and sodium chloride are used to make the enzyme alcohol oxidase stable at room temperature for months.

The method for impregnation is by dipping the absorbent material in the liquid composition or by flowing the liquid in a controlled manner onto the absorbent surface. Once the long plastic sheets containing the impregnated absorbent material are dry then they are cut into strips 0.5 cm. wide. This device which is approximately 5 cm. long and 0.5 cm wide can be used to quantify or detect ethanol. To quantify a sample for ethanol the strip is either dipped into the sample or the sample is placed on the device in such a way that the absorbent material can absorb some of the sample being tested.

The indicator O-tolidine and the FDC yellow #5 dye enables a color spectrum to be produced that range from yellow through light green to a very blue-green. Each of the various green shades appears with different ethanol concentrations or different reaction times. This level of ethanol in the unknown sample can be found when the color of the impregnated absorbent material is compared with a color chart having blocks representing specific ethanol levels. The period for the reaction time must be held constant when using this method. An alternate method for determining the ethanol level of a sample is to determine the period of time that is necessary for the impregnated absorbent material to become a specified color. This time is then compared with a time chart having various reaction times that are necessary to cause a specific shade of green. These times represent specific ethanol levels and are used to determine the ethanol concentration of the sample.

The method described for preparing the ethanol testing device is suitable for determining ethanol levels in samples that are not heavily colored. The testing device must be further processed if it is to be used for colored colloidal material, solutions containing colored high molecular weight material or colored cellular material (blood). The purpose of this added process is to prevent the colored sample substance or other molecules or particulates from entering the absorbent material. This process involves covering the surface of the impregnated material with a semipermeable transparent coating film such as ethyl cellulose, regenerated cellulose or other absorbent material. This coating will prevent interfering material from entering the reaction site. Ethyl cellulose (1.25% w/v) can be dissolved in a suitable solvent and applied to the surface of the testing material then dried.

This proposed device can be used for detecting ethanol or quantifying ethanol from various samples. For example a specific use for this ethanol testing device is to estimate ethanol blood levels from saliva ethanol samples. This can be done by placing a small volume of saliva from a person who consumed ethanol on the absorbent material. The color reaction is allowed to proceed to indicate the amount of ethanol that is present in the saliva. The ethanol level in the sample is found by comparing the color of the sample after a specified time to a color chart representing ethanol concentrations and reaction times. This salivary ethanol level was found to correlate closely with blood ethanol levels and breath alcohol levels found by an intoxilyzer. This device has not been found to falsely react with saliva that did not contain ethanol.

What is claimed is:

1. A method for determining the level of ethanol in a fluid or air comprising exposing absorbent material to said fluid or air, the absorbent material being impregnated with a composition comprising:
    (a) An indicator solution comprising orthotolidine, a yellow dye, ethanol and tris(hydroxymethy)-aminomethane/sodium phosphate buffer solution and
    (b) an enzyme solution comprising dextran, sodium chloride, peroxidase, alcohol oxidase, semicarbazide hydrochloride and a tris(hydroxymethyl)-aminomethane/sodium phosphate buffer solution said dextran and sodium chloride being present in amounts sufficient to stabilize the alcohol oxidase and the semicarbazide hydrchloride being present in an amount sufficient to inhibit said alcohol oxidase.

2. The method of claim 1 wherein the indicator solution comprises:
    Ortho-tolidine: 0.002% to 20% by weight
    dye: 0.001% to 50% by weight
    ethanol: 0.5% to 95% by weight
    buffer solution (pH 5 to 10): 0.01% to 70% by weight
and the enzyme solution comprises:
    dextran: 0.02% to 50% by weight
    sodium chloride: 0.02% to 20% by weight
    peroxidase (95 units/mg): 0.001% to 20% to weight
    alcohol oxidase (35 units/mg)*: 0.001% to 40% by weight
    semicarbazide hydrochloride: 0.02% to 3% by weight
    buffer solution (pH 5 to 10): 0.01% to 75% by weight
*one unit=the amount of enzyme to oxidize 1.0 uMole methanol to formaldehyde per minute at pH 7.5 at 25° C.

3. The method of claim 1 wherein said indicator solution comprises 0.1 g ortho-tolidine, 0.042 g FDC yellow No. 5 dye, 2 ml ethanol (95% v/v) and 23 ml buffer solution of pH 8.0 and said enzyme solution comprises 232 units peroxidase, 140 units alcohol oxidase, 0.15 g dextran, 0.018 g sodium chloride, 0.0123 g semicarbazide hydrochloride in a total volume of 2 ml buffer solution at pH 8.0.

4. The method of claim 3 wherein dextran has a molecular weight of 40,000.

5. A composition of making ethanol detection strips comprising dextran, sodium chloride, peroxidase, alcohol oxidase, semicarbazide, a buffer solution and a hydrogen peroxide detecting reagent said dextran and sodium chloride being present in amounts sufficient to stabilize the alcohol oxidase and the semicarbazide hydrochloride being present in an amount sufficient to inhibit said alcohol oxidase.

6. The composition of claim 5 wherein the components are present in the indicated amounts:
    dextran: 0.02% to 50% by weight
    sodium chloride: 0.02% to 20% by weight
    peroxidase (95 units/mg): 0.001% to 20% by weight
    alcohol oxidase (35 units/mg)*: 0.0001% to 40% by weight
    semicarbazide hydrochloride: 0.02% to 3% by weight
    buffer solution (pH 5 to 10): 0.01% to 75% by weight
*one unit=the amount of enzyme to oxidize 1.0 uMole ethanol to formaldehyde per minute at pH 7.5 at 25° C.

7. The composition of claim 5 comprising 232 units peroxidase, 140 units alcohol oxidase, 0.15 g dextran, 0.018 g sodium chloride, 0.0123 g semicarbazide hydrochloride in a total volume of 2 ml buffer solution at pH 8.0.

8. A composition of claim 7 wherein said dextran has a molecular weight of 40,000.

* * * * *